(12) United States Patent
Park et al.

(10) Patent No.: US 10,328,902 B2
(45) Date of Patent: Jun. 25, 2019

(54) RAIN SENSOR, VEHICLE USING THE SAME, AND METHOD FOR CONTROLLING THE VEHICLE

(71) Applicants: Hyundai Motor Company, Seoul (KR); Kia Motors Corporation, Seoul (KR); Hyundai Autron Co., Ltd., Seongnam, Gyeonggi-do (KR)

(72) Inventors: Jong Min Park, Incheon (KR); Nak Kyoung Kong, Gyeonggi-do (KR); Ki Hong Lee, Seoul (KR); Keun Sig Lim, Gyeonggi-do (KR); Young Ik Cho, Gyeonggi-do (KR); KyungTaek Kim, Gyeonggi-do (KR); WonBok Hong, Gyeonggi-do (KR); Taewang Kim, Gyeonggi-do (KR)

(73) Assignees: Hyundai Motor Company, Seoul (KR); Kia Motors Corporation, Seoul (KR); Hyundai Autron Co., Ltd., Seongnam, Gyeonggi-do (KR)

( * ) Notice: Subject to any disclaimer, the term of this patent is extended or adjusted under 35 U.S.C. 154(b) by 0 days.

(21) Appl. No.: 15/675,723

(22) Filed: Aug. 12, 2017

(65) Prior Publication Data
US 2018/0170316 A1 Jun. 21, 2018

(30) Foreign Application Priority Data
Dec. 20, 2016 (KR) .......................... 10-2016-0174352

(51) Int. Cl.
*G01J 4/00* (2006.01)
*B60S 1/08* (2006.01)
*G01N 21/45* (2006.01)

(52) U.S. Cl.
CPC ............ *B60S 1/0833* (2013.01); *G01N 21/45* (2013.01)

(58) Field of Classification Search
CPC ...... G01N 21/21; G01N 21/211; G01N 21/23; G01J 4/04; G01J 4/00
USPC ....................................................... 356/364
See application file for complete search history.

(56) References Cited

U.S. PATENT DOCUMENTS

| 6,153,995 A | 11/2000 | Tanaka |
| 7,002,480 B2 | 2/2006 | Kobayashi et al. |
| 7,034,932 B2 | 4/2006 | Kobayashi et al. |
| 8,941,835 B2 | 1/2015 | Hirai et al. |
| 2002/0148738 A1* | 10/2002 | Boyd ...................... G01N 33/32 205/782 |
| 2004/0144911 A1* | 7/2004 | Stam ....................... B60Q 1/143 250/208.1 |

(Continued)

FOREIGN PATENT DOCUMENTS

JP H1062336 A 3/1998

*Primary Examiner* — Md M Rahman
(74) *Attorney, Agent, or Firm* — Mintz Levin Cohn Ferris Glovsky and Popeo, P.C.; Peter F. Corless

(57) ABSTRACT

A rain sensor is included in a vehicle, and a method for controlling the vehicle utilizes the rain sensor. The rain sensor includes a light transmitter configured to radiate light to a windshield of the vehicle; a light receiver configured to receive light reflected from the windshield to generate a reception light signal; a filter configured to filter out noise from the reception light signal; and a controller configured to determine a presence or absence of pollutant and a degree of pollution on the basis of the filtered reception light signal, and perform pollutant removing.

7 Claims, 17 Drawing Sheets

(56) References Cited

U.S. PATENT DOCUMENTS

| | | | |
|---|---|---|---|
| 2012/0097099 A1* | 4/2012 | Roeckle | B65G 49/0459 |
| | | | 118/423 |
| 2013/0222115 A1* | 8/2013 | Davoodi | H04Q 9/00 |
| | | | 340/10.1 |
| 2014/0319866 A1* | 10/2014 | Freitag | B60P 3/224 |
| | | | 296/24.32 |
| 2015/0142209 A1* | 5/2015 | Breed | G08G 1/096716 |
| | | | 701/1 |
| 2017/0030716 A1* | 2/2017 | Ali | G06K 9/00355 |
| 2017/0120931 A1* | 5/2017 | An | B60W 50/10 |

* cited by examiner

RAIN SENSOR, VEHICLE USING THE SAME, AND METHOD FOR CONTROLLING THE VEHICLE

CROSS-REFERENCE TO RELATED APPLICATION

This application claims under 35 U.S.C. § 119(a) the benefit of Korean Patent Application No. 10-2016-0174352, filed on Dec. 20, 2016 in the Korean Intellectual Property Office, the entire contents of which are incorporated by reference herein.

BACKGROUND

1. Technical Field

The present disclosure relates to a rain sensor, a vehicle using the same, and a method for controlling the vehicle.

2. Description of the Related Art

Recently, many developers and companies have conducted research into development of various additional service devices for vehicles and methods for installing such additional service devices into vehicles in consideration of user convenience and safety of vehicle occupants.

In particular, the additional service devices for vehicles may include not only a safety assistant device such as a lane departure warning device that provides steering assistance to prevent a vehicle from deviating from a traveling lane during driving, but also an additional service device such as a navigation device that provides a route to a user-selected destination and peripheral information on the route.

Dust or dirt may be attached to a windshield of the vehicle due to external environmental factors such as weather during driving, or the windshield of the vehicle may be polluted by various foreign substances or dust because the windshield is exposed to the outside.

In particular, the windshield needs to guarantee the driver's field of vision and/or must remain clear for autonomous traveling in which the vehicle autonomously recognizes obstacles located in a forward direction of the vehicle and a peripheral traveling environment, such that a clean windshield must be maintained for safe driving.

SUMMARY

Therefore, it is an aspect of the present disclosure to provide a rain sensor for continuously monitoring a state of a windshield so as to maintain the windshield in a clean state, a vehicle using the same, and a method for controlling the vehicle.

Additional aspects of the invention will be set forth in part in the description which follows and, in part, will be apparent from the description, or may be learned by practice of the invention.

In accordance with an aspect of the present disclosure, a rain sensor includes: a light transmitter configured to radiate light to a windshield of a vehicle; a light receiver configured to receive a light reflected from the windshield to generate a reception light signal; a filter configured to filter out noise from the reception light signal; and a controller configured to determine a presence or absence of pollutant and a degree of pollution on the basis of the filtered reception light signal, and perform pollutant removing.

The light transmitter may include a total reflection light transmitter and a diffused reflection light transmitter.

During short-term monitoring, the controller may compare each of the amount of total-reflection reception light, which is received from the total reflection light transmitter and reflected, and the amount of diffused-reflection reception light, which is received from the diffused reflection light transmitter and reflected, with the amount of normal reception light of a normal state, so as to detect a difference among the amount of total reflection reception light, the amount of diffused-reflection reception light, and the amount of normal reception light, and may detect an outdoor temperature, thereby detecting the presence or absence of the pollutant on the basis of the detected difference and the detected outdoor temperature.

The pollutant may include at least one of muddy water, snow, ice, dust and/or oil film.

The controller may long-term monitor the amount of total reflection reception light transmitted and reflected from the total reflection light transmitter and the amount of diffused reflection reception light transmitted and reflected from the diffused reflection light transmitter, and mat perform pollutant removing by reflecting the pollution degree when the pollution degree is equal to or higher than a reference value.

The controller may determine the pollution degree by determining the pollution degree by long-term monitoring the amount of total reflection reception light and the amount of diffused reflection reception light, and may correct a rainwater sensing reference value according to the determined pollution degree.

The controller may store the long-term monitoring result of the total reflection reception light and the diffused reflection reception light, may compare the amount of reception light before starting the vehicle with the amount of reception light after starting the vehicle so as to determine the pollution degree, and may perform pollutant removing according to the determined result.

After completion of a wiping operation, if the amount of total reflection reception light transmitted and reflected from the total reflection light transmitter does not reach a reference value and is reduced by an offset, the controller may determine that wiper blades needs to be replaced, and may perform wiper blade replacement notification.

If the vehicle equipped with the rain sensor is an autonomous traveling mode, the controller may determine the presence or absence of the pollutant and the degree of pollution, and may perform pollutant removing according to the determined result.

In accordance with another aspect of the present disclosure, a vehicle includes: a rain sensor configured to monitor the amount of total reflection reception light and the amount of diffused reflection reception light reflected from a windshield, detect a pollutant from the windshield and a degree of pollution, and perform pollutant removing according to the detected result; and a body control module (BCM) configured to control a corresponding structure according to a pollutant removal request signal received from the rain sensor.

The vehicle may further include: a heating element configured to emit heat to the windshield; a washer configured to spray a washer fluid onto the windshield; a wiper configured to remove the pollutant from the windshield; and an air conditioner configured to blow air onto the windshield.

If the pollutant is muddy water, the body control module (BCM) may operate the washer and the wiper according to the pollutant removal request signal.

If the pollutant is snow, the body control module (BCM) may operate the heating element and the air conditioner according to the pollutant removal request signal, and then operates the wiper.

If the pollutant is ice, the body control module (BCM) may operate the heating element and the air conditioner according to the pollutant removal request signal, may wait for a predetermined time, and may operate the wiper.

After completion of a wiping action of the wiper, if the amount of total reflection reception light does not reach a reference value and is reduced by an offset, the rain sensor may determine that wiper blades need to be replaced, and may notify the body control module (BCM) of wiper blade replacement.

The vehicle may further include: a cluster display; and a lamp, wherein the body control module (BCM) is configured to display information regarding wiper blade replacement notification received from the rain sensor through the cluster display or the lamp.

In accordance with still another aspect of the present disclosure, a method for controlling a vehicle includes: if an ignition signal (IGN) of a vehicle is turned on, determining whether a current state is an automatic rain sensing state; if the automatic rain sensing state is determined, calculating a change amount of total reflection reception light and a change amount of diffused reflection reception light; determining the presence or absence of pollutant on the basis of the calculation result; and if the presence of pollutant is determined, performing pollutant removing.

The vehicle may include a washer and a wiper. The performing the pollutant removing may include: if the pollutant is muddy water, removing the muddy water by operating the washer and the wiper.

The vehicle may include a heating element, an air conditioner, and a wiper. The performing the pollutant removing may include: if the pollutant is snow, operating the heating element and the air conditioner, and operating the wiper.

The vehicle may include a heating element, an air conditioner, and a wiper. The performing the pollutant removing may include: if the pollutant is ice, operating the heating element and the air conditioner, waiting for a predetermined time, and operating the wiper.

The method may further include: after performing the pollutant removing, after completion of a wiping action, if the amount of total reflection reception light does not reach a reference value and is reduced by an offset, determining that wiper blades need to be replaced, and notifying wiper blade replacement.

The method may further include: prior to determining whether the current state is the automatic rain sensing state after the vehicle ignition signal is turned on, determining whether a current mode is an autonomous traveling mode. If the autonomous traveling mode is determined, the method may include calculating a change amount of total reflection reception light and a change amount of diffused reflection reception light. If the autonomous traveling mode is not determined, the method may include determining whether a current state is the automatic rain sensing state.

In accordance with another aspect of the present disclosure, a method for controlling a vehicle includes: if an ignition signal (IGN) of a vehicle is turned on, determining whether a current state is an automatic rain sensing state; if the automatic rain sensing state is determined, determining the presence or absence of an initial ignition signal; if the initial ignition signal is not determined, calculating a change amount of total reflection reception light and a change amount of diffused reflection reception light; calculating a degree of pollution on the basis of the calculated result; determining whether a current state is a polluted state on the basis of the calculated pollution degree; and if the polluted state is determined, performing pollutant removing.

If the initial ignition signal is determined according to the result of determining the presence or absence of the initial ignition signal, when a change amount of the total reflection reception light and a change amount of the diffused reflection reception light are calculated, the method may further include calculating the change amount of total reflection reception light obtained before and after vehicle starting and the change amount of diffused reflection reception light obtained before and after vehicle starting; and when the pollution degree is calculated, calculating a pollution degree before vehicle starting and a pollution degree after vehicle starting.

The vehicle may include a washer and a wiper, wherein the performing the pollutant removing includes operating the washer and the wiper.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
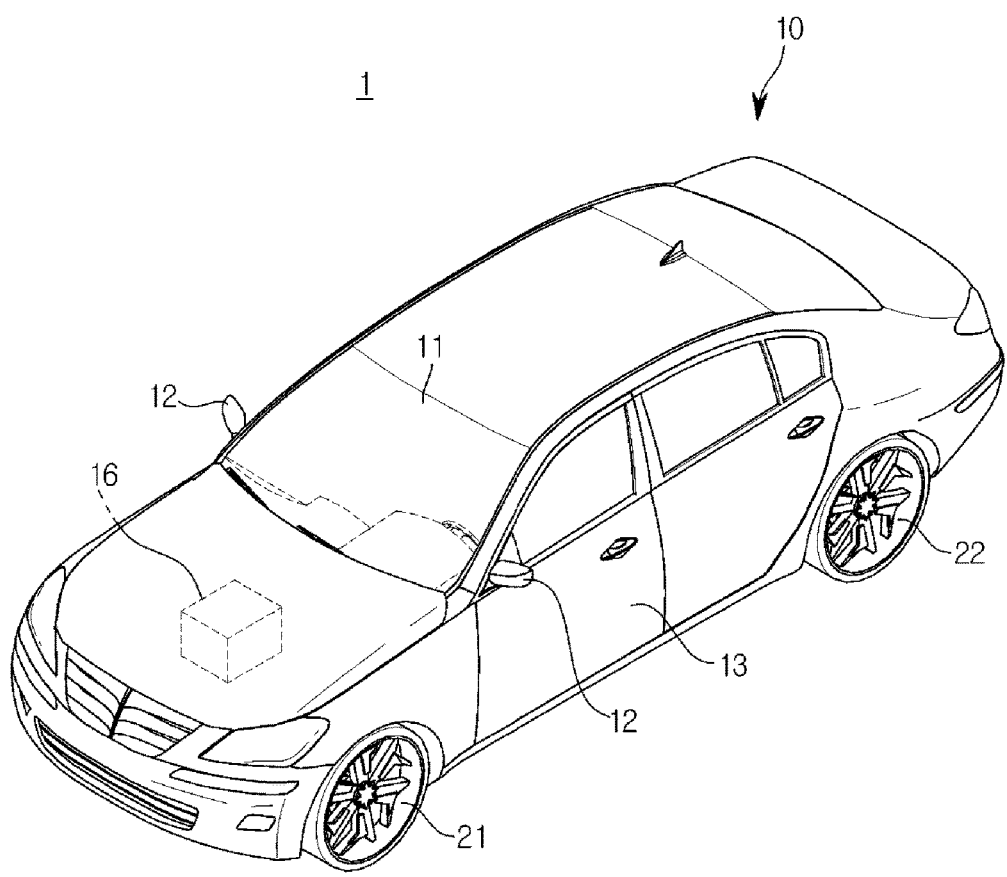
FIG. 1 is a perspective view illustrating the appearance of a vehicle according to an embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Reference will now be made in detail to the embodiments of the present disclosure, examples of which are illustrated in the accompanying drawings, wherein like reference numerals refer to like elements throughout. It should be noted that the specification of the present disclosure does not describe all the constituent elements of the embodiments, and general matters well known to those skilled in the art and redundant matters of the embodiments will not be described herein for clarity.

The principles of the present disclosure and the embodiments of the present disclosure will hereinafter be described with reference to the attached drawings.

FIG. 1 is a perspective view illustrating the appearance of a vehicle according to an embodiment of the present disclosure.

Referring to FIG. 1, the vehicle 1 includes a main body 10 forming the appearance of the vehicle 1, a windshield 11 to provide a forward view of the vehicle 1 to a vehicle driver who drives the vehicle 1, side-view mirrors 12 to provide a rear view of the vehicle 1 to the vehicle driver, doors 13 to shield an indoor space of the vehicle 1 from the outside, and wheels 21 and 22 including front wheels 21 provided at the front of the vehicle 1 and rear wheels 22 provided at the rear of the vehicle 1 in a manner that the vehicle 1 moves forward or backward.

The windshield 11 is provided at a front upper portion of the main body 10 so that a vehicle driver who drives the vehicle 1 can obtain visual information of a forward direction of the vehicle 1. The windshield 11 may also be referred to as a windshield glass or a windscreen. The side-view mirrors 12 may include a left side-view mirror provided at the left of the main body 10 and a right side-view mirror provided at the right of the main body 10, so that the driver who drives the vehicle 1 can obtain visual information of the lateral and rear directions of the vehicle 1.

The doors 13 are rotatably provided at the right and left sides of the main body 10 so that a vehicle driver can ride in the vehicle 1 when any of the doors 13 is open and an indoor space of the vehicle 1 can be shielded from the outside when the doors 13 are closed.

In addition to the above-mentioned constituent elements, the vehicle 1 may further include a power system 16 to rotate wheels 21 and 22, a steering system (not shown) to steer the vehicle 1, and a brake system (not shown) to stop movement of the wheels 21 and 22.

The power system 16 may provide rotational force to the front wheels 21 or the rear wheels 22 in a manner that the main body 10 moves forward or backward. The power system 16 may include an engine to generate rotational force by burning fossil fuels or a motor to generate rotational force upon receiving a power source from a condenser (not shown).

The steering system may include a steering wheel 42 (see FIG. 2) to receive a travel direction from the vehicle driver, a steering gear (not shown) to convert the rotary motion of the steering wheel 42 into the reciprocating motion, and a steering link (not shown) to deliver the reciprocating motion of the steering gear (not shown) to the front wheels 21. The steering system may change the direction of each rotation axis of the wheels 21 and 22, such that the vehicle 1 can be steered.

The brake system may include a brake pedal (not shown) to receive braking manipulation from the vehicle driver, a brake drum (not shown) coupled to the wheels 21 and 22, and a brake shoe (not shown) to brake rotation of the brake drum (not shown) using frictional force. The brake system stops rotation of the wheels 21 and 22, such that it can brake traveling or running of the vehicle 1.

Figure 2:
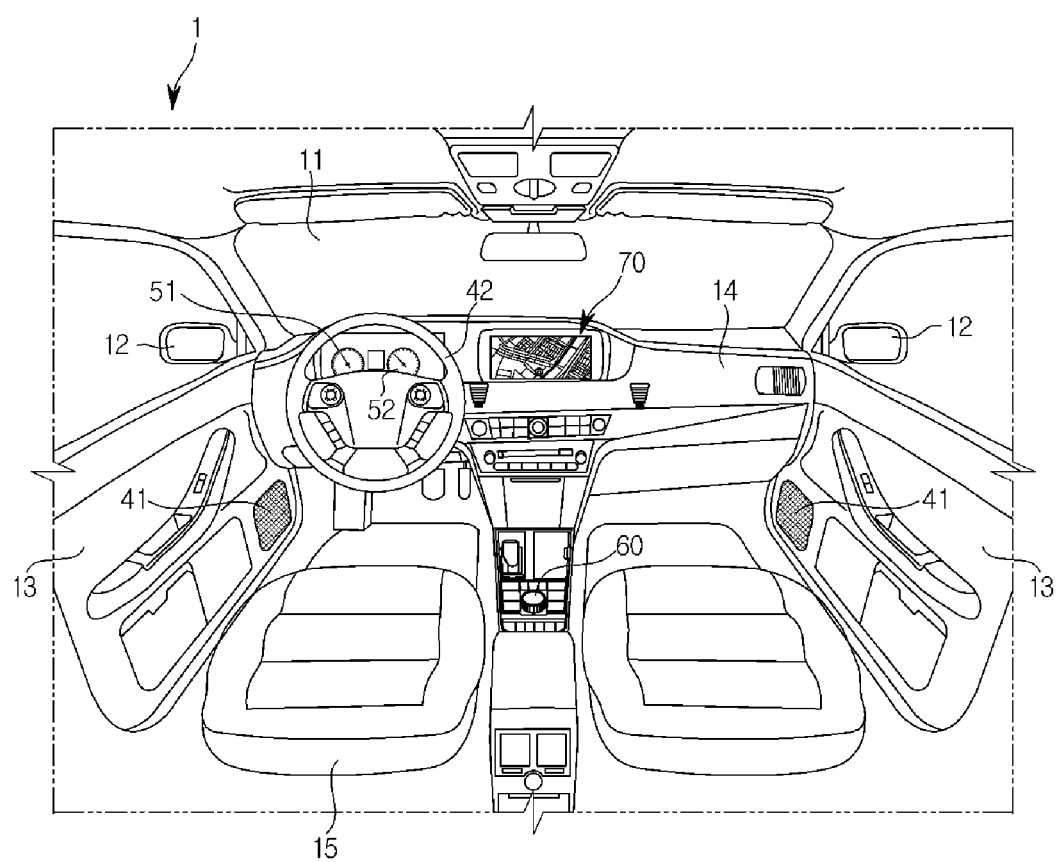
FIG. 2 is a schematic view illustrating the internal structure of the vehicle according to an embodiment of the present disclosure.

FIG. 2 is a schematic view illustrating the internal structure of the vehicle according to an embodiment of the present disclosure.

Referring to FIG. 2, the interior structure of the vehicle 1 may include a dashboard 14 having a plurality of electronic components needed for the vehicle driver who manipulates the vehicle 1, a driver seat 15 for the driver of the vehicle 1; cluster displays 51 and 52 configured to display operation information of the vehicle 1, and a navigation device 70 configured to provide navigation information and audio/video (AV) functions upon receiving a command from the vehicle driver.

The dashboard 14 may protrude from a lower part of the windshield 11 toward the vehicle driver, such that the vehicle driver who looks forward can manipulate various devices mounted to the dashboard 14 using the dashboard 14.

The driver seat 15 is provided at the rear of the dashboard 14, such that the vehicle driver who has a stable carriage or posture can drive the vehicle 1 while viewing various devices of the dashboard 14.

The cluster displays 51 and 52 located adjacent to the driver seat 15 of the dashboard 14 may include a speed gauge 51 for displaying a traveling speed of the vehicle 1, and an RPM gauge 52 for displaying a rotation speed of a power system (not shown).

The navigation device 70 may include a display for displaying a navigation function configured to provide information of a road on which the vehicle 1 travels or a route to a destination desired by the vehicle driver, and a speaker 41 to output sound according to a command of the driver.

In recent times, an Audio Video Navigation (AVN) device 60 including an audio device, a video device, and a navigation device has been widely installed in vehicles. The navigation device 70 may be installed in a center fascia (or center console).

The center fascia may be a control panel, which is located between the driver seat and the passenger seat, in the dashboard 14. The dashboard 14 and a shift lever are perpendicular to each other at the center fascia. The center fascia region may include the navigation device 70, a controller for an audio system, air-conditioner, and heater, an air vent (i.e., an air outlet), a cigar jack, an ashtray, a cup holder, etc. The center fascia may include a center console such that it serves to separate the driver seat and the passenger seat from each other.

In addition, the center fascia may include the navigation device 70 and a jog dial 60 needed to manipulate various operations of the vehicle.

A user (i.e., a vehicle driver) may perform necessary operations by rotating or pressing the jog dial 60. A touchpad having a touch recognition function may be used, such that the touch pad may perform handwriting recognition requisite for drive manipulation using a user's finger or a tool having a separate touch recognition function.

Figure 3:
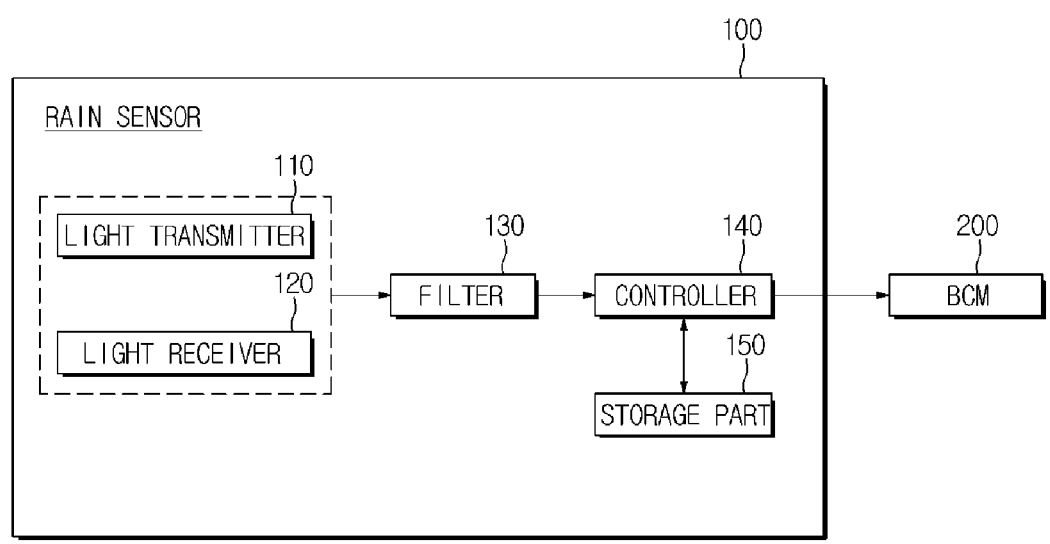
FIG. 3 is a block diagram illustrating constituent elements of a rain sensor.

FIG. 3 is a block diagram illustrating a rain sensor.

Figure 5:
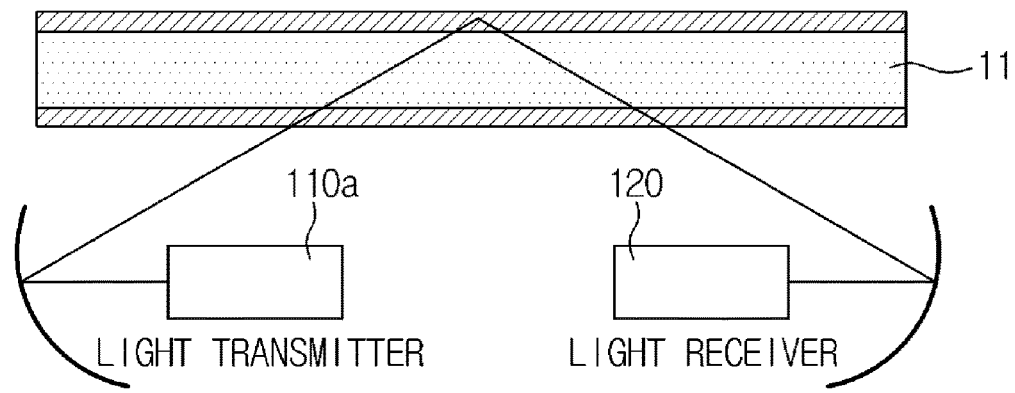
FIGS. 5 and 6 are conceptual diagrams illustrating a total-reflection light transceiver applied to the vehicle.
Figure 6:
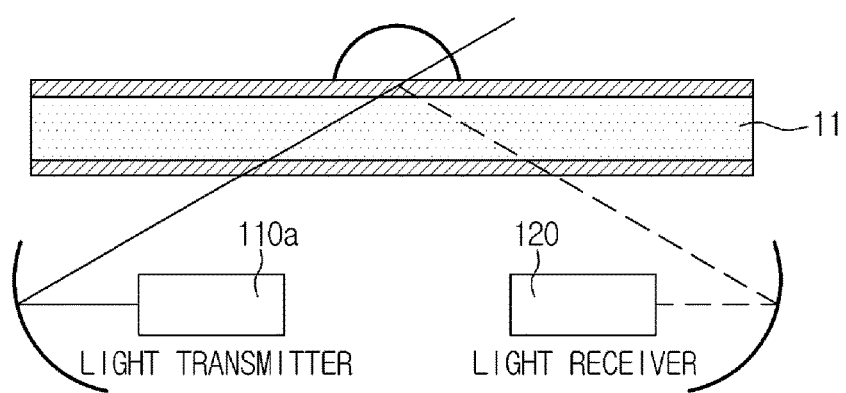
Figure 7:
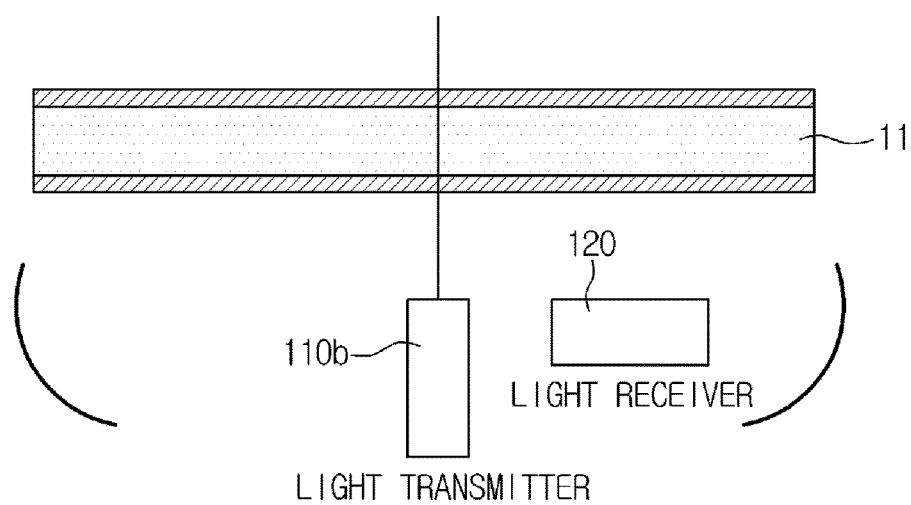
FIGS. 7 and 8 are conceptual diagrams illustrating a diffused-reflection light transceiver applied to the vehicle.
Figure 8:
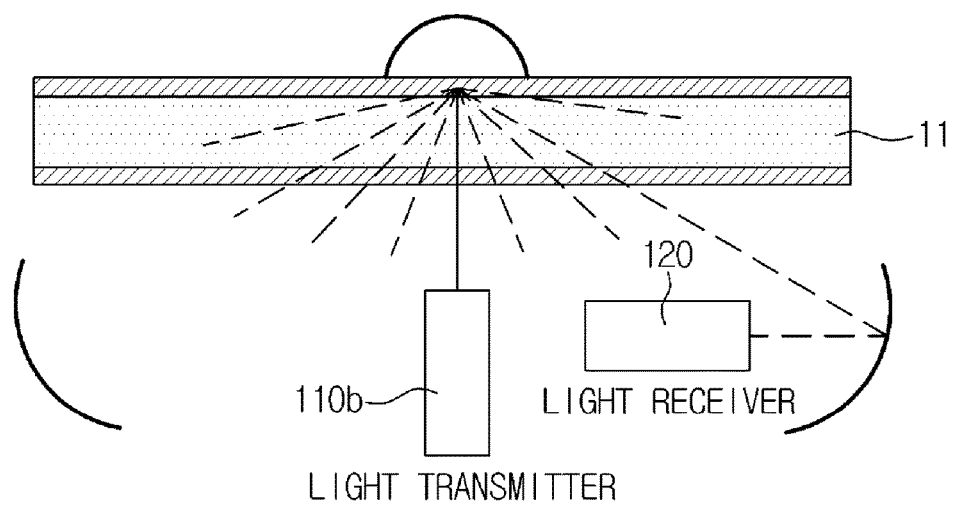
Figure 9:
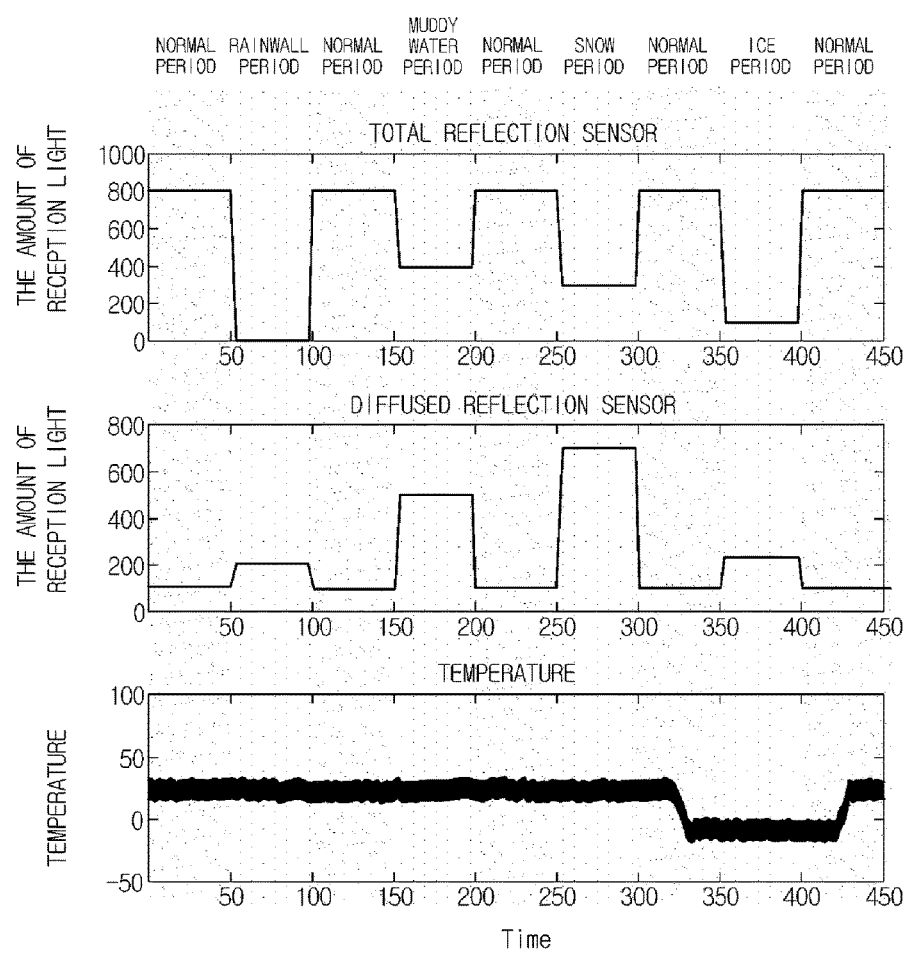
FIG. 9 is a view illustrating an example of a method for detecting foreign substances.
Figure 10:
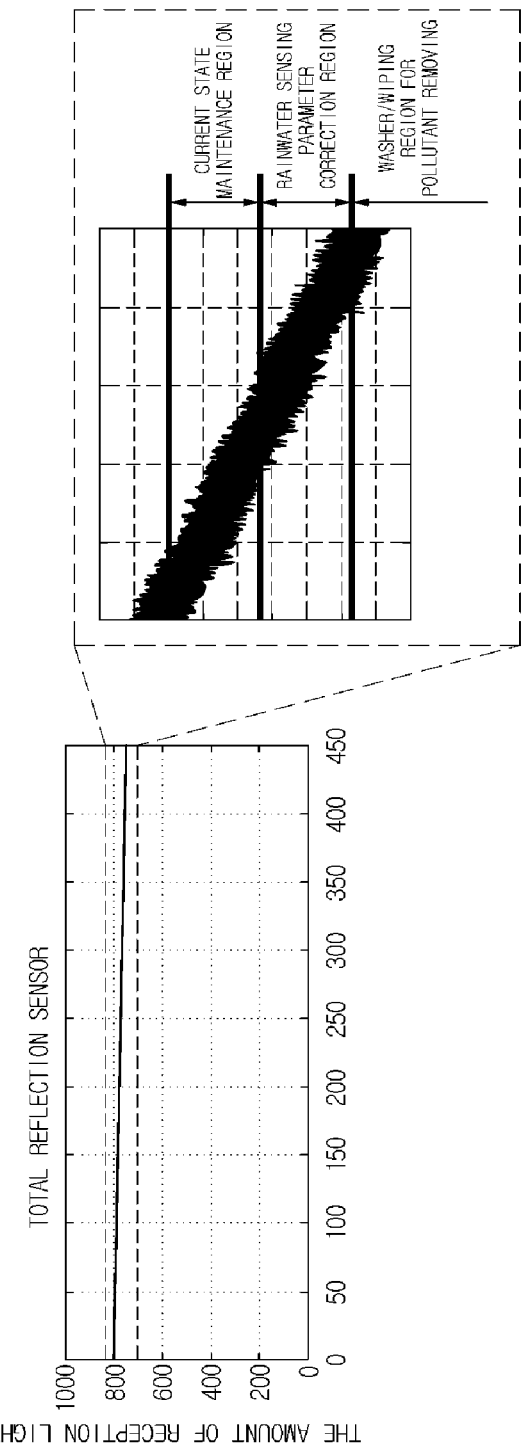
FIGS. 10 and 11 are graphs illustrating a method for determining the degree of pollution.
Figure 11:
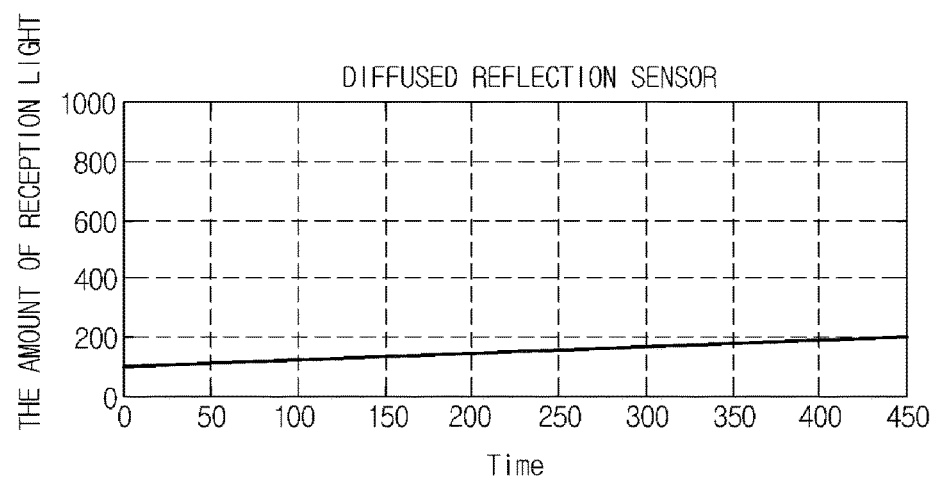
Figure 12:
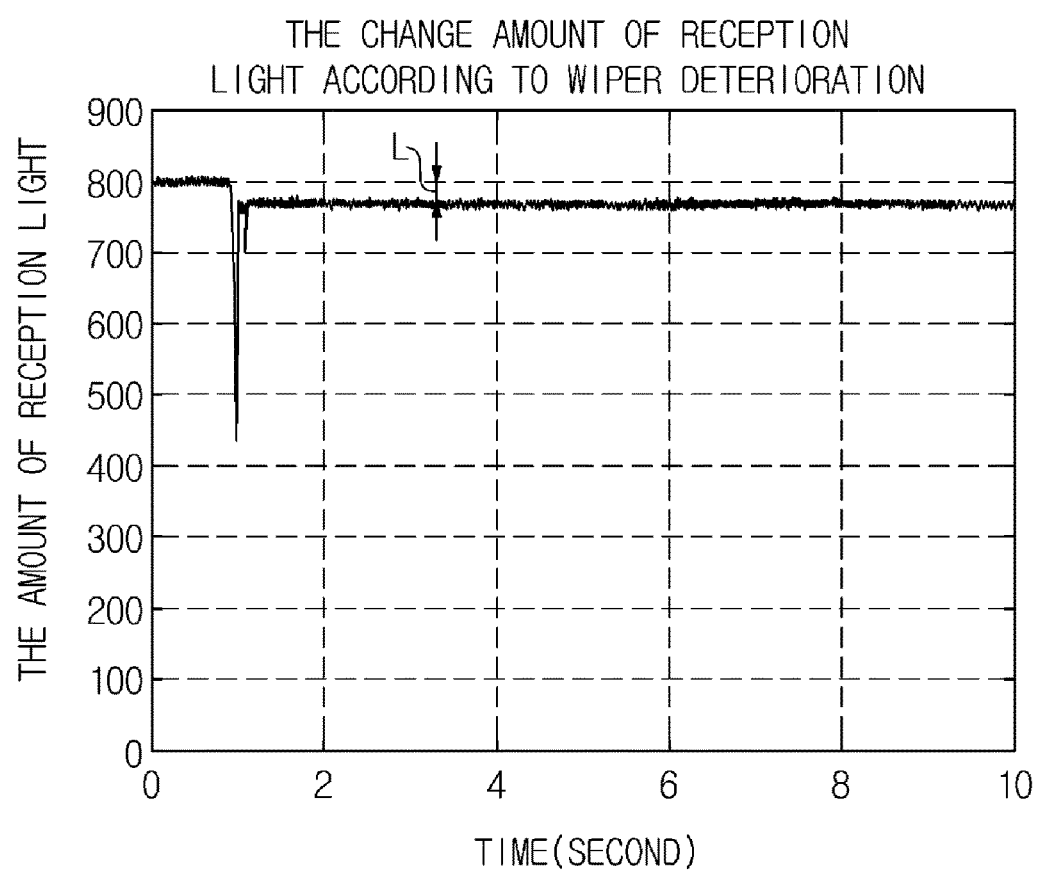
FIG. 12 is a graph illustrating a method for determining whether wiper blades need to be replaced.

FIGS. 5 and 6 are conceptual diagrams illustrating a total-reflection light transceiver applied to the vehicle. FIGS. 7 and 8 are conceptual diagrams illustrating a diffused-reflection light transceiver applied to the vehicle. FIG. 9 is a view illustrating an example of a method for detecting foreign substances or pollutants. FIGS. 10 and 11 are graphs illustrating a method for determining the degree of pollution. FIG. 12 is a graph illustrating a method for determining whether wiper blades need to be replaced.

Referring to FIG. 3, the rain sensor 100 may include a light transmitter 110, a light receiver 120, a filter 130, a controller 140, and a storage part 150.

The light transmitter 110 may radiate light to the windshield 11 (see FIG. 2) of the vehicle 1 (see FIG. 2).

The light transmitter 110 may include a total-reflection light transmitter and a diffused-reflection light transmitter.

The light receiver 120 may generate a light reception signal upon receiving light reflected from the windshield 11.

The filter 130 may filter the light reception signal. In this case, the filter 130 may perform analog signal processing of the light reception signal received through the light receiver 120, and may filter out noise needed to recognize the amount of received light.

The controller 140 may determine the presence or absence of foreign substances and the degree of pollution on the basis of the filtered light reception signal, and may control the foreign substances to be removed. The foreign substances may include at least one of muddy water, snow, ice, dust, and oil film, without being limited thereto. The foreign substances may include all kinds of materials capable of polluting the windshield 11.

In particular, during short-term monitoring, the controller 140 may compare each of the amount of total-reflection reception light, which is received from the total-reflection light transmitter and reflected, and the amount of diffused-reflection reception light, which is received from the diffused-reflection light transmitter and reflected, with the amount of reception light of a normal state, so as to detect a difference among the amount of total-reflection reception light, the amount of diffused-reflection reception light, and the amount of normal reception light, and may detect an outdoor temperature. As a result, through short-term monitoring, the controller 140 may recognize the presence or absence of foreign substances on the basis of the detected difference and the detected outdoor temperature. In this case, the short-term monitoring may be defined as a monitoring operation shorter than long-term monitoring to be described later.

Referring to FIGS. 5 and 6, assuming that the light transmitter 110 is a total-reflection light transmitter 110a, when foreign substances are not attached to the windshield 111 as shown in FIG. 5, all light emitted from the total-reflection light transmitter 110a is reflected from the windshield 11, such that a large amount of reception light applied to the light receiver 120 occurs. In contrast, assuming that the light transmitter 110 is the total-reflection light transmitter 110a, when foreign substances are attached to the windshield 11 as shown in FIG. 6, all or some of light emitted from the total-reflection light transmitter 110a may be reflected from the windshield 11, such that the amount of reception light applied to the light receiver 120 is smaller than the amount of reception light generated in a normal state having no foreign substances.

Referring to FIGS. 7 and 8, assuming that the light transmitter 110 is a diffused-reflection light transmitter 110b, when foreign substances are not attached to the windshield 111 as shown in FIG. 7, all light emitted from the diffused-reflection light transmitter 110b penetrates the windshield 11 and does not arrive at the light receiver 120. In contrast, assuming that the light transmitter 110 is the diffused-reflection light transmitter 110b, when foreign substances are attached to the windshield 111 as shown in FIG. 8, light emitted from the diffused-reflection light transmitter 110b is reflected from the windshield 11 such that the amount of reception light applied to the light receiver 120 increases. The amount of total-reflection reception light and the amount of diffused-reflection reception light may be complementary to each other.

Referring to the amount of reception light illustrated in FIG. 9, a normal period is a predetermined time in which no rainwater and no foreign substances are detected. A rainwater period is a predetermined time in which the amount of reception light of the light receiver 120 is changed by rainwater. In the rainwater period, the amount of total-reflection reception light is gradually reduced and approximates to zero "0", and the amount of diffused-reflection reception light is slightly increased by light scattered by rainwater as compared to the amount of total-reflection reception light. A muddy water period is a predetermined time in which the amount of reception light of the light receiver 120 is changed by muddy water. In the muddy water period, the amount of total-reflection reception light is slightly reduced according to a density of muddy water, and is then maintained. In the muddy water period, although the amount of diffused-reflection reception light is increased with different rates according to the density of muddy water, the increased amount of diffused-reflection reception light is then maintained. A snow period is a predetermined time in which the amount of reception light of the light receiver 120 is changed by snow. In the snow period, the amount of total-reflection reception light may be reduced by a predetermined rate and then maintained, and the amount of diffused-reflection reception light may increase to a relatively high value. An ice period is a predetermined time in which the amount of reception light of the light receiver 120 is changed by ice. In the ice period, the amount of total-reflection reception light is gradually reduced and approximates to zero "0", and the amount of diffused-reflection reception light is slightly increased by light scattered by ice.

In this case, it may be difficult to discriminate between the rainwater period and the ice period on the basis of the amount of total-reflection reception light and the amount of diffused-reflection reception light.

The controller 140 may determine the presence or absence of foreign substances on the windshield 11 on the basis of the above-mentioned total reflection and diffused-reflection principles. Since it is difficult to discriminate between the rainwater period and the ice period on the basis of the amount of total-reflection reception light and the amount of diffused-reflection reception light, the controller 140 may discriminate between rainwater and ice.

In particular, the controller 160 may use the amount of reception light and the outdoor temperature to discriminate between the rainwater period and the ice period. If the outdoor temperature is a degree above zero, the rainwater period may be decided. Unless the outdoor temperature is the degree above zero, the ice period may be decided.

During an autonomous traveling mode, the controller 140 may determine the presence or absence of foreign substances irrespective of an automatic rain sensing mode, may operate heating elements, an air conditioner, a washer, and a wiper of the vehicle according to the determined result, and may thus provide a vehicle driver with an optimum field of vision (or view).

The controller 140 may monitor the amount of total-reflection reception light and the amount of diffused-reflection reception light through long-term monitoring, and may sense that the windshield 11 is gradually polluted. When the degree of pollution reaches a reference value, the controller 140 may determine that the windshield 11 is polluted, and may thus automatically remove such pollution. In this case, the long-term monitoring may be defined as a monitoring operation longer than the short-term monitoring.

In particular, during long-term monitoring, the controller 140 may monitor the amount of total-reflection reception light, which is received from the total-reflection light transmitter and reflected, and the amount of diffused-reflection reception light, which is received from the diffused-reflection reception light transmitter and reflected. If the degree of pollution is equal to or higher than a reference value, the controller 140 may remove such pollution on the basis of the degree of pollution.

Referring to FIGS. 10 and 11, after lapse of a time, the windshield 11 is polluted such that it is confirmed that the amount of total-reflection reception light is gradually reduced and the amount of diffused-reflection reception light is gradually increased. Upon receiving the result of long-term monitoring, the controller 140 may determine a polluted state when the amount of total-reflection reception light and the amount of diffused-reflection reception light arrive at a washer and wiping region for pollutant removal, such that the controller 140 may transmit a control signal needed for pollutant removal to a body control module (BCM) 200.

In addition, the controller 140 may determine the degree of pollution by long-term monitoring the amount of total-reflection reception light and the amount of diffused-reflection reception light, and may correct a reference value for rainwater sensing according to the determined pollution degree. For example, when the amount of total-reflection reception light arrives at a rainwater sensing parameter correction region of FIG. 10, the controller 140 may correct the rainwater sensing reference value to more correctly perform rainwater sensing, such that the controller 140 can prevent the rainwater sensing level from being underestimated or overestimated according to the pollution degree such that the wiper is prevented from being wiped more rapidly or more slowly than the actual amount of rainwater.

The controller 140 may store the long-term monitoring result of the amount of total-reflection reception light and the amount of diffused-reflection reception light, may compare the amount of reception light before starting the vehicle and the amount of reception light after starting the vehicle to determine the degree of pollution, and may perform pollutant removal according to the determined pollution degree.

Referring to FIG. 12, when the amount of total-reflection reception light, which is received from the light transmitter and reflected after completion of the wiping action, does not reach a reference value and is reduced by an offset L, the controller 140 may determine that the wiper blades need to be replaced and may inform the vehicle driver of wiper blade replacement.

When the vehicle 1 equipped with the rain sensor is in the autonomous traveling mode, the controller 140 may first determine the presence or absence of foreign substances and the degree of pollution, and may remove pollutants according to the determined result. As a result, in the autonomous traveling mode, the controller 140 can prevent any forward obstacle and peripheral traffic conditions of the vehicle 1 from being undetected under the condition that a clear field of view is not guaranteed due to pollution of the windshield 11.

The storage part 150 may store various kinds of information related to the rain sensor 100, for example, reference values needed for foreign substance detection, pollution level decision, wiper blade replacement decision, and rainwater sensing reference value adjustment decision. However, the scope or spirit of various kinds of information is not limited thereto.

Although the storage part 150 may be implemented as any one of a non-volatile memory (e.g., a cache, a Read Only Memory (ROM), a Programmable ROM (PROM), an Erasable Programmable ROM (EPROM), an Electrically Erasable Programmable ROM (EEPROM), a flash memory, etc.), a volatile memory (e.g., a Random Access Memory (RAM)), and a storage medium (e.g., a Hard Disk Drive (HDD), a CD-ROM, etc.), the scope or spirit of the present disclosure is not limited thereto. The storage part 150 may be a memory that is implemented as a separate chip independent of the above processor related to the controller 140, or may be implemented as a processor and a single chip.

Figure 4:
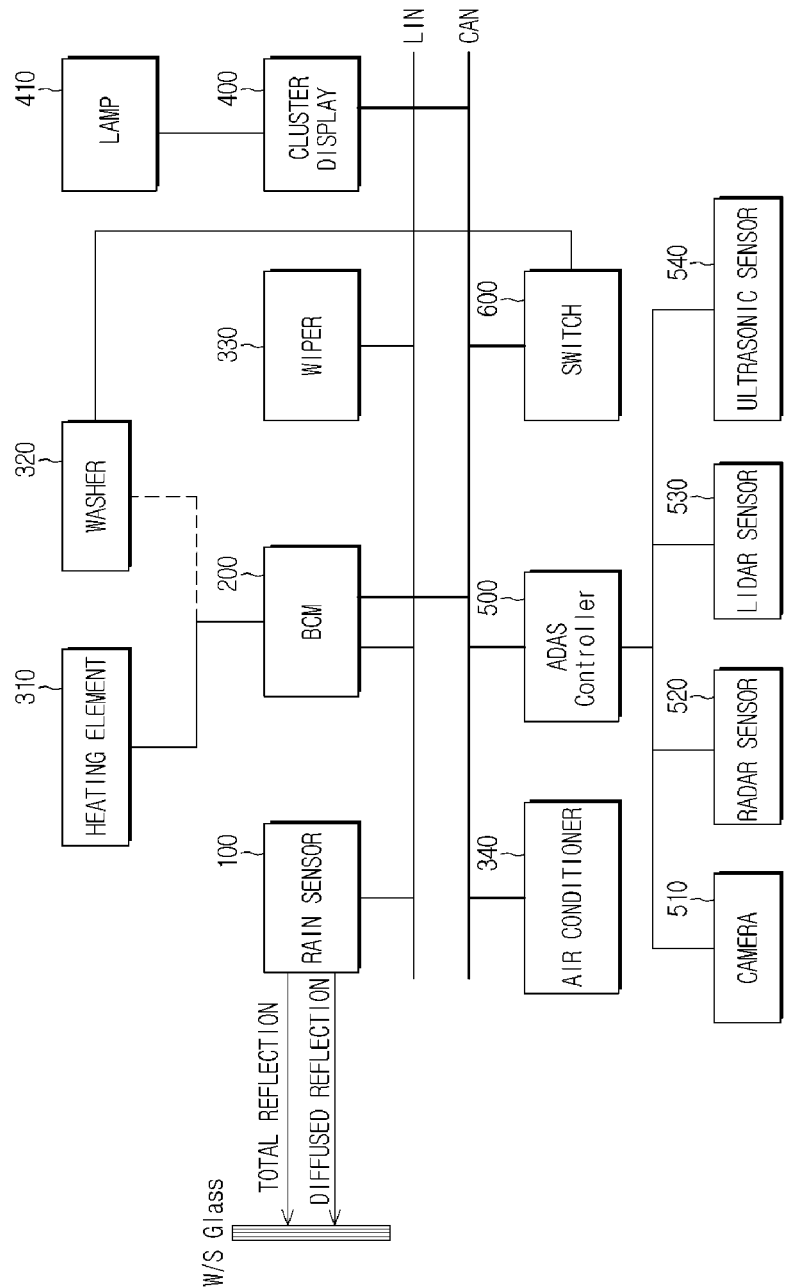
FIG. 4 is a block diagram illustrating constituent elements of the vehicle.

FIG. 4 is a block diagram illustrating constituent elements of the vehicle.

Referring to FIG. 4, the vehicle 1 may include a rain sensor 100, a body control module (BCM) 200, a heating element (also called a heating line) 310, a washer 320, a wiper 330, an air conditioner 340, a cluster display 400, a lamp 410, an advanced driver assistance system (ADAS) 500, and a switch 600.

Referring to FIG. 4, the rain sensor 100, the BCM 200, and the wiper 330 may be coupled to one another over a Local Interconnect Network (LIN). The BCN 200 may be connected to the air conditioner 340, the ADAS 500, the switch 600, and the cluster display 400 over a Controller Area Network (CAN). The BCM 200 may be connected to the heating element 310 and the washer 320. Here, the washer 320 may also be connected to the switch 600 instead of the BCM 200. The cluster display 400 may be connected to the lamp 410.

The ADAS 500 may be connected to a camera 510, a radar sensor 520, a lidar sensor 530, and an ultrasonic sensor 540.

The rain sensor 100 may monitor the amount of total-reflection reception light and the amount of diffused-reflection reception light reflected from the windshield 11 of FIG. 2, may detect foreign substances attached to the windshield 11 and the degree of pollution according to the monitoring result, and may remove pollutants according to the detection result.

After completion of the wiping action, if the total reflection reception light does not reach a reference value and is reduced by an offset, the rain sensor 100 may determine that the wiper blades need to be replaced and may inform the BCM 200 of the determined wiper blade replacement.

The BCM 200 may control the corresponding constituent element according to a pollutant removal request signal received from the rain sensor.

If the foreign substance or pollutant is muddy water, the BCM 200 may operate the washer 320 and the wiper 330 according to the pollutant removal request signal.

If the foreign substance or pollutant is snow, the BCM 200 may operate the heating element 310 and the air conditioner 340 according to the pollutant removal request signal, and may then operate the wiper 330.

If the foreign substance or pollutant is ice, the BCM 200 may operate the heating element 310 and the air conditioner 340 according to the pollutant removal request signal, may wait for a predetermined time, and may then operate the wiper 330.

The BCM 200 may display information regarding wiper blade replacement received from the rain sensor 100 on the display 400 or through the lamp 410.

The BCM 200 may be implemented as an algorithm for controlling the constituent elements contained in the vehicle 1, a memory (not shown) for storing data regarding a program implementing the algorithm, and a processor (not shown) for performing the above-mentioned operation using data stored in the memory. In this case, the memory and the processor may be implemented as different chips as necessary. Alternatively, the memory and the processor may be implemented as a single chip.

The heating element 310 may be configured to heat the windshield 11. The heating element 310 may be contained in the windshield 11 to emit heat.

The washer 320 may be configured to spray a washer fluid onto the windshield 11. The washer 320 may spray the washer fluid onto the windshield 11 through a nozzle.

The wiper 330 may be configured to remove foreign substances or pollutants from the windshield 11. The wiper 330 may remove rainwater and pollutants flowing down to the windshield of the vehicle 1, and may remove pollutants or rainwater by wiping the windshield surface using the wiper blade.

The air conditioner 340 may be configured to blow air onto the windshield 11.

The cluster display 400 and the lamp 410 may inform the vehicle driver or user of wiper blade replacement, but the scope or spirit of the present disclosure is not limited thereto. All kinds of constituent elements capable of informing the vehicle driver of various kinds of information generated in the vehicle 1 can also be applied to the embodiments of the present disclosure without departing from the scope or spirit of the present disclosure.

The ADAS 500 may receive vehicle traveling state monitoring information from the camera 510, the radar sensor 520, the lidar sensor 530, and the ultrasonic sensor 540, may recognize a vehicle traveling state, may generate various kinds of information needed for vehicle traveling, and may provide the generated information.

The switch 600 may operate the wiper 330 and the washer 320.

As described above, the BCM 200 may remove foreign substances and pollutants from the windshield 11 through cooperation among various constituent elements contained in the vehicle 1 upon receiving a control signal from the rain sensor 100. In this case, a reference for removing pollutants according to categories of foreign substances may be transmitted from the rain sensor 100 to the BCM 200. Alternatively, the pollutant removal reference may be shared and stored between the rain sensor 100 and the BCM 200 prior to removing the foreign substances or pollutants. When the rain sensor 100 transmits information regarding the type of foreign substance or the polluted state, the BCM 200 may also operate the corresponding structure according to the pre stored removal reference.

Although not shown in the drawings, the vehicle 1 may further include a communication part, an input part, and a display without departing from the scope or spirit of the present disclosure.

The communication part may include one or more constituent elements capable of communicating with the external device. For example, the communication part may include at least one of a short-range communication module, a wired communication module, and a wireless communication module.

The short-range communication module may include a variety of short-range communication modules for transmitting/receiving signals over a wireless communication network over a short distance, for example, a Bluetooth module, an infrared communication module, a Wireless Local Access Network (WLAN) communication module, a Near Field Communication (NFC) communication module, a ZigBee communication module, etc.

The wired communication module may include not only various wired communication modules, for example, a Controller Area Network (CAN) communication module, a Local Area Network (LAN) module, a Wide Area Network (WAN) module, a Value Added Network (VAN) module, etc., but also various cable communication modules, for example, Universal Serial Bus (USB), High Definition Multimedia Interface (HDMI), Digital Visual Interface (DVI), RS-232 (recommended standard232), power line communication, a Plain Old Telephone Service (POTS), etc.

The wireless communication module may include various wired communication modules, for example, a Radio Data System-Traffic Message Channel (RDS-TMC) module, a Digital Multimedia Broadcasting (DMB) module, a Wi-Fi module, and a Wireless broadband (WiBro) module, and may further include a wireless communication module for supporting various wireless communication schemes, for example, Global System for Mobile Communication (GSM), Code Division Multiple Access (CDMA), Wideband Code Division Multiple Access (WCDMA), Universal Mobile Telecommunications System (UMTS), Time Division Multiple Access (TDMA), Long Term Evolution (LTE), etc.

The wireless communication module may include a wireless communication interface comprised of an antenna and a receiver configured to receive a traffic information signal. The wireless communication module may further include a traffic information signal conversion module configured to demodulate an analog-type radio signal received through the wireless communication interface into a digital control signal.

The input part may include hardware devices, for example, various buttons or switches for user input, a pedal, a keyboard, a mouse, a track ball, various levers, a handle, a stick, etc.

The input part may be implemented as a graphical user interface (GUI) such as a touchpad for user input. That is, the input part may include a software input device such as a GUI. The touchpad may be implemented as a touch screen panel (TSP). The TSP and the display may construct a mutual layer structure.

The display may be implemented by any one of a Cathode Ray Tube (CRT), a Digital Light Processing (DLP) panel, a Plasma Display Panel (PDP), a Liquid Crystal Display (LCD) panel, an Electro Luminescence (EL) panel, an Electrophoretic Display (EPD) panel, an Electrochromic Display (ECD) panel, a Light Emitting Diode (LED) panel, and an Organic Light Emitting Diode (OLED) panel, without being limited thereto.

Figure 13:
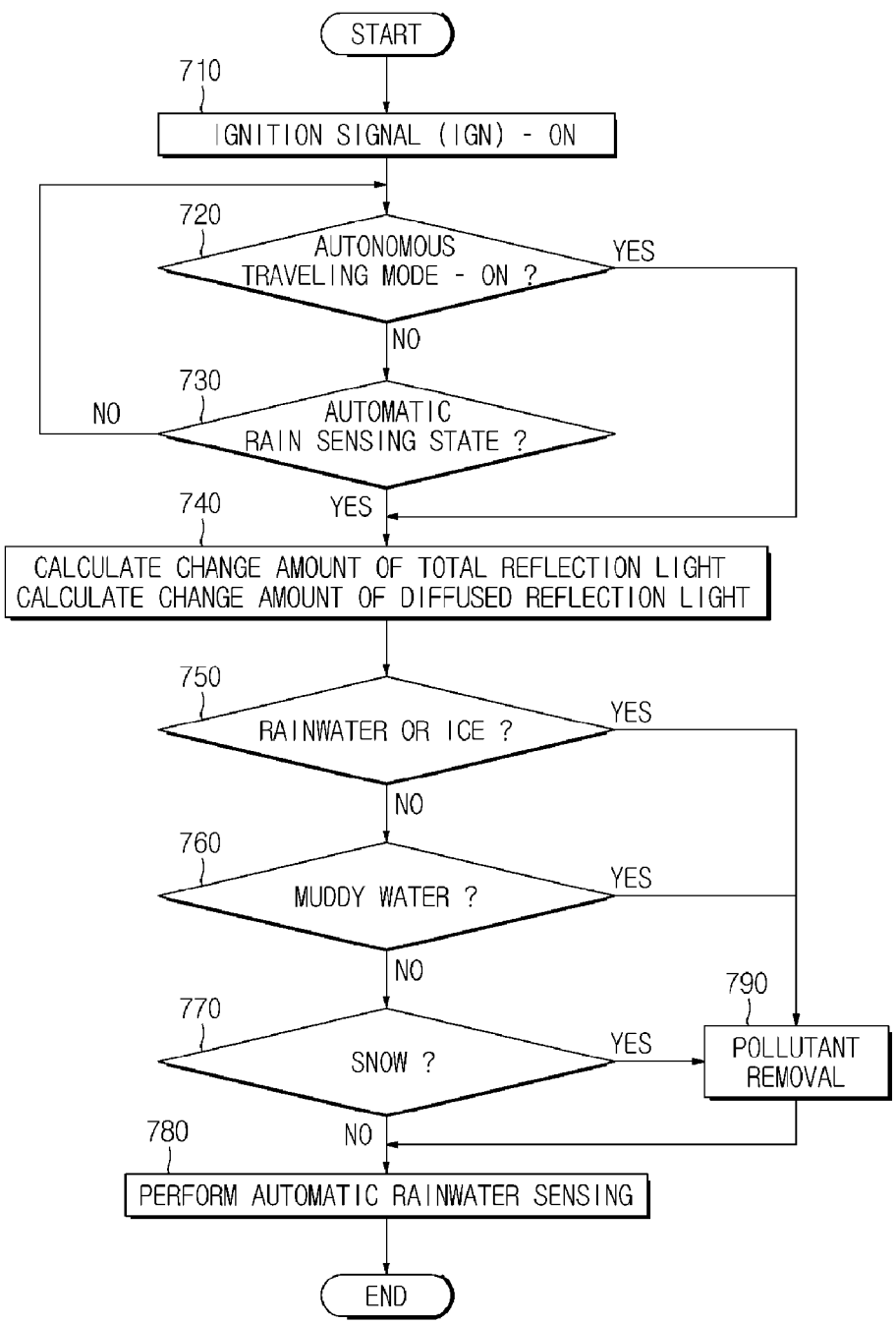
FIGS. 13 and 14 are flowcharts illustrating methods for detecting foreign substances.
Figure 14:
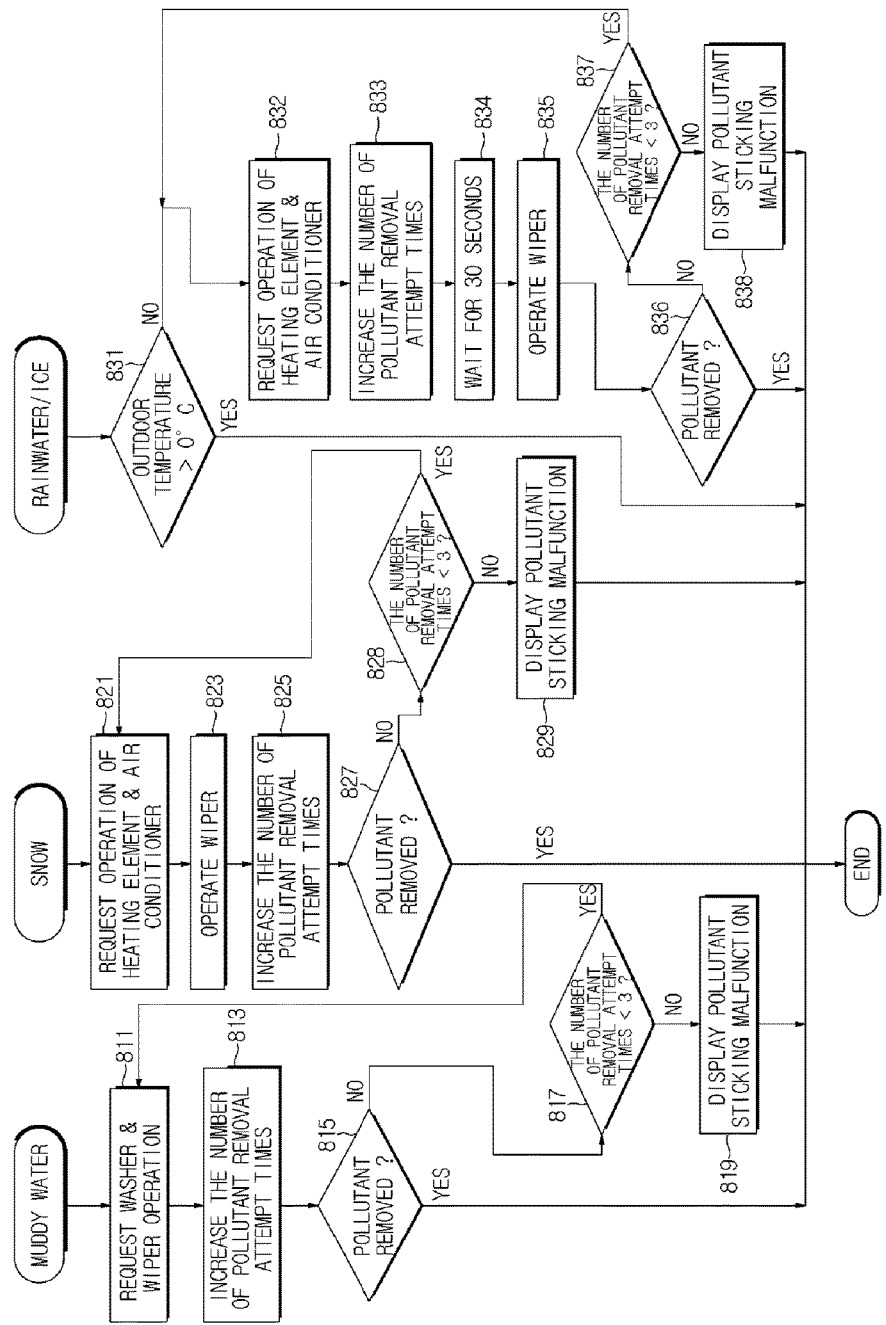

FIGS. 13 and 14 are flowcharts illustrating methods for detecting foreign substances.

Referring to FIG. 13, when an ignition signal IGN of the vehicle 1 is turned on (Operation 710), it is determined whether a current mode is an autonomous traveling mode (Operation 720). In this case, the operation 720 for determining whether a current mode is the autonomous traveling mode may herein be omitted according to the necessity of operators or administrators.

If the current mode is not identical to the autonomous traveling mode (Operation 720), the vehicle 1 may determine whether an automatic rain sensing state is decided (Operation 730). The operation 730 may be determined according to whether or not the washer 320 and the wiper 330 of the switch 600 are automatically established. If driving of the washer 320 and the wiper 330 of the switch 600 is automatically established, the automatic rain sensing state may be decided.

If the automatic rain sensing state is decided (Operation 730), the vehicle 1 may calculate the change amount of total-reflection reception light and the change amount of diffused-reflection reception light (Operation 740).

Subsequently, the vehicle 1 may determine the presence or absence of foreign substances or pollutants on the basis of the calculation result (Operations 750 to 770).

In particular, the vehicle 1 may determine whether the foreign substance or pollutant is rainwater or ice according to the references of FIG. 9 upon receiving the change amount of total-reflection reception light and the change amount of diffused-reflection reception light (Operation 750). If the rainwater or ice is not decided, the vehicle 1 may determine whether the foreign substance or pollutant is muddy water (Operation 760). If muddy water is not decided, it is determined whether the foreign substance or pollutant is snow (Operation 770) such that the presence or absence of foreign substances or pollutants may be decided. In this case, a reference for deciding the type of foreign substance or pollutant may be decided at random by operators or administers.

If the foreign substance or pollutant is not detected, the vehicle 1 may automatically sense or detect the rainwater (Operation 780).

If the foreign substance or pollutant is present (Operations 750 to 770), the vehicle 1 may remove the foreign substance or pollutant (Operation 790).

Although not shown in the drawings, after completion of the wiping operation for pollutant removal (Operation 790), if the amount of total-reflection reception light does not reach a reference value and is reduced by an offset, the vehicle 1 may determine the wiper blades need to be replaced, and may inform the vehicle driver of the need for wiper blade replacement.

If the autonomous traveling mode is decided (Operation 720), the vehicle 1 may start from the operation 740 for calculating the change amount of total-reflection reception light and the change amount of diffused-reflection reception light.

FIG. 14 is a flowchart illustrating the operation 790 for removing foreign substances or pollutants of FIG. 13.

Referring to FIG. 14, if the foreign substance is muddy water, the vehicle 1 may remove the muddy water by operating the washer 320 and the wiper 330 (Operation 811). For this purpose, the vehicle 1 may include the washer 320 and the wiper 330.

Subsequently, the vehicle 1 may increase the number of pollutant removal attempt times (Operation 813), and may confirm whether pollutants are completely removed on the basis of the amount of reception light of the light receiver 120 (Operation 815). For example, if the amount of reception light is equal to or higher than a reference value when the light transmitter is a total-reflection light transmitter, and if the amount of reception light is equal to or less than a reference value or is zero "0" when the light transmitter is a diffused-reflection light transmitter, the vehicle 1 may determine that pollutants have been completely removed.

If the pollutants are not completely removed, the vehicle 1 may determine whether the number of pollutant removal attempt times is less than a reference number of times (e.g., three times) (Operation 817).

If the number of pollutant removal attempt times is less than the reference number of times, the vehicle 1 may start from the operation 811.

If the number of pollutant removal attempt times is higher than the reference number of times, the vehicle 1 may display information indicating a malfunction of pollutant sticking so that the vehicle driver can recognize the malfunction of the pollutant sticking (Operation 819).

In this case, the vehicle 1 may display information regarding the malfunction of pollutant sticking through the cluster display 400 (see FIG. 4) or the lamp 410 (see FIG. 4), and the scope or spirit of the present disclosure is not limited thereto. All kinds of structures capable of audibly or visually informing the vehicle driver who rides in the vehicle 1 of such malfunction information may be applied to the embodiments without departing from the scope or spirit of the present disclosure.

Referring to FIG. 14, when the pollutant is snow, the vehicle 1 may operate the heating element 310 and the air conditioner 340 (Operation 821), and may operate the wiper 330 (Operation 823). For this purpose, the vehicle 1 may also include the heating element 310, the air conditioner 340, and the wiper 330 without departing from the scope or spirit of the present disclosure.

Thereafter, the vehicle 1 may increase the number of pollutant removal attempt times (Operation 825), and may confirm whether pollutants are completely removed on the basis of the amount of reception light of the light receiver 120 (Operation 827). For example, if the amount of reception light is equal to or higher than a reference value when the light transmitter is a total-reflection light transmitter, and if the amount of reception light is equal to or less than a reference value or is zero "0" when the light transmitter is a diffused-reflection light transmitter, the vehicle 1 may determine that pollutants have been completely removed.

If the pollutants are not completely removed, the vehicle 1 may determine whether the number of pollutant removal attempt times is less than a reference number of times (e.g., three times) (Operation 828).

If the number of pollutant removal attempt times is less than the reference number of times, the vehicle 1 may restart (or resume) from the operation 821.

If the number of pollutant removal attempt times is higher than a reference number of times, the vehicle 1 may display information regarding a malfunction of pollutant sticking such that the vehicle driver can recognize such malfunction information (Operation 829).

Referring to FIG. 14, if the pollutant is rainwater or ice, the vehicle 1 may determine whether the outdoor temperature is a degree above zero (Operation 831).

If the outdoor temperature is not set to the degree above zero, the vehicle 1 may determine that the pollutant is ice and may then perform a subsequent operation.

If the pollutant is ice, the vehicle 1 may operate the heating element 310 and the air conditioner 340, may wait for a predetermined time (e.g., 30 seconds), and may operate the wiper 330. To this end, the vehicle 1 may also include the heating element 310, the air conditioner 340, and the wiper 330 without departing from the scope or spirit of the present disclosure.

In particular, the vehicle 1 may operate the heating element 310 and the air conditioner 340 (Operation 832), may increase the number of pollutant removal attempt times (Operation 833), may wait for a predetermined time (e.g., 30 seconds) (Operation 834), and may operate the wiper 330 (Operation 835).

Subsequently, the vehicle 1 may determine whether pollutants are completely removed on the basis of the amount of reception light of the light receiver 120 (Operation 836). For example, if the amount of reception light is equal to or higher than a reference value when the light transmitter is a total-reflection light transmitter, and if the amount of reception light is equal to or less than a reference value or is zero "0" when the light transmitter is a diffused-reflection light transmitter, the vehicle 1 may determine that pollutants have been completely removed.

If the pollutants are not completely removed, the vehicle 1 may determine whether the number of pollutant removal attempt times is less than a reference number of times (e.g., three times) (Operation 837).

If the number of pollutant removal attempt times is less than the reference number of times, the vehicle 1 may restart (or resume) from the operation 832.

If the number of pollutant removal attempt times is higher than a reference number of times, the vehicle 1 may display information regarding a malfunction of pollutant sticking such that the vehicle driver can recognize such malfunction information (Operation 838).

If the outdoor temperature is the degree above zero (Operation 831), the vehicle 1 may determine that the pollutant is rainwater, such that the vehicle 1 may perform the automatic rainwater sensing execution operation 780 of FIG. 13.

Figure 15:
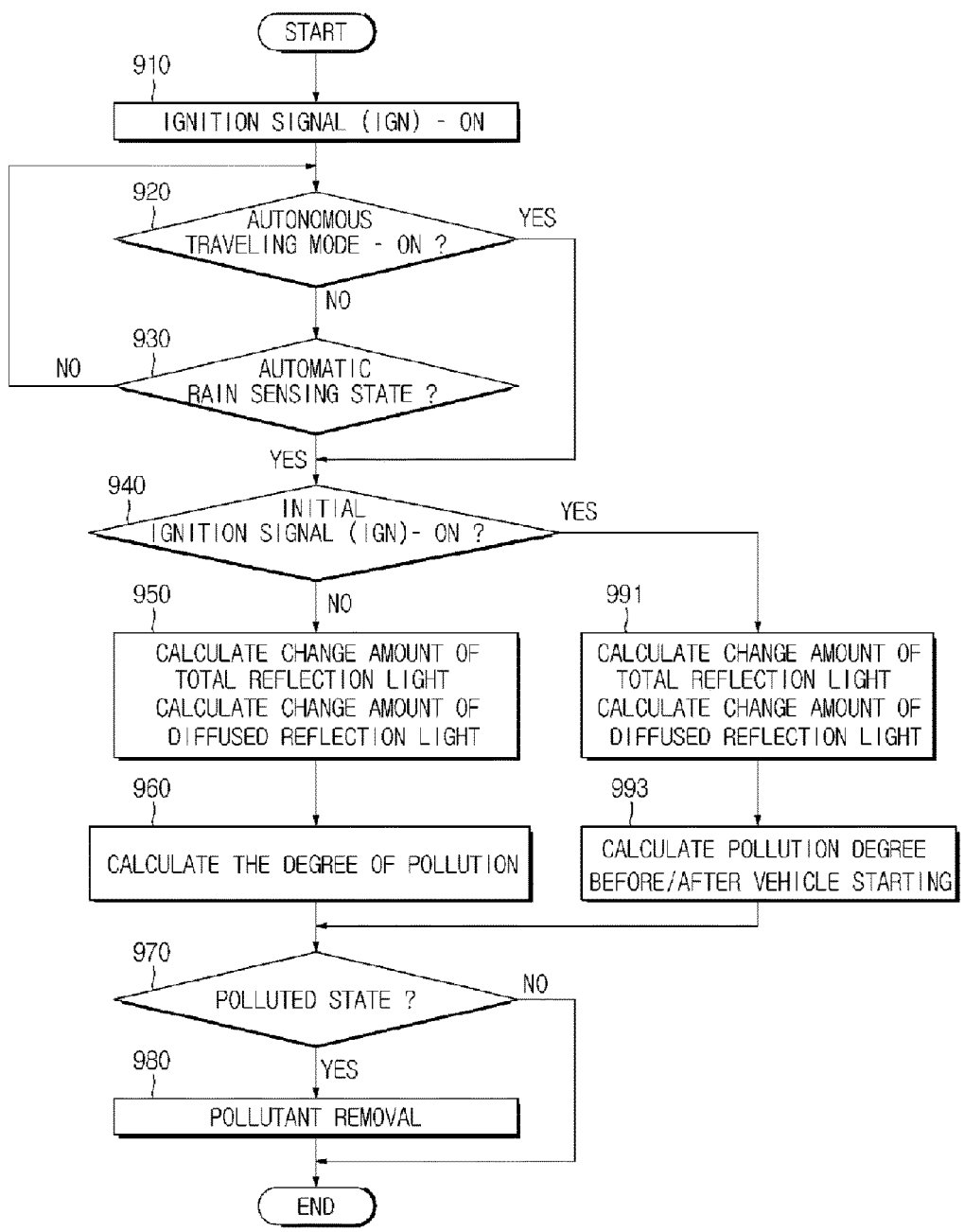
FIGS. 15 and 16 are flowcharts illustrating methods for determining the degree of pollution.
Figure 16:
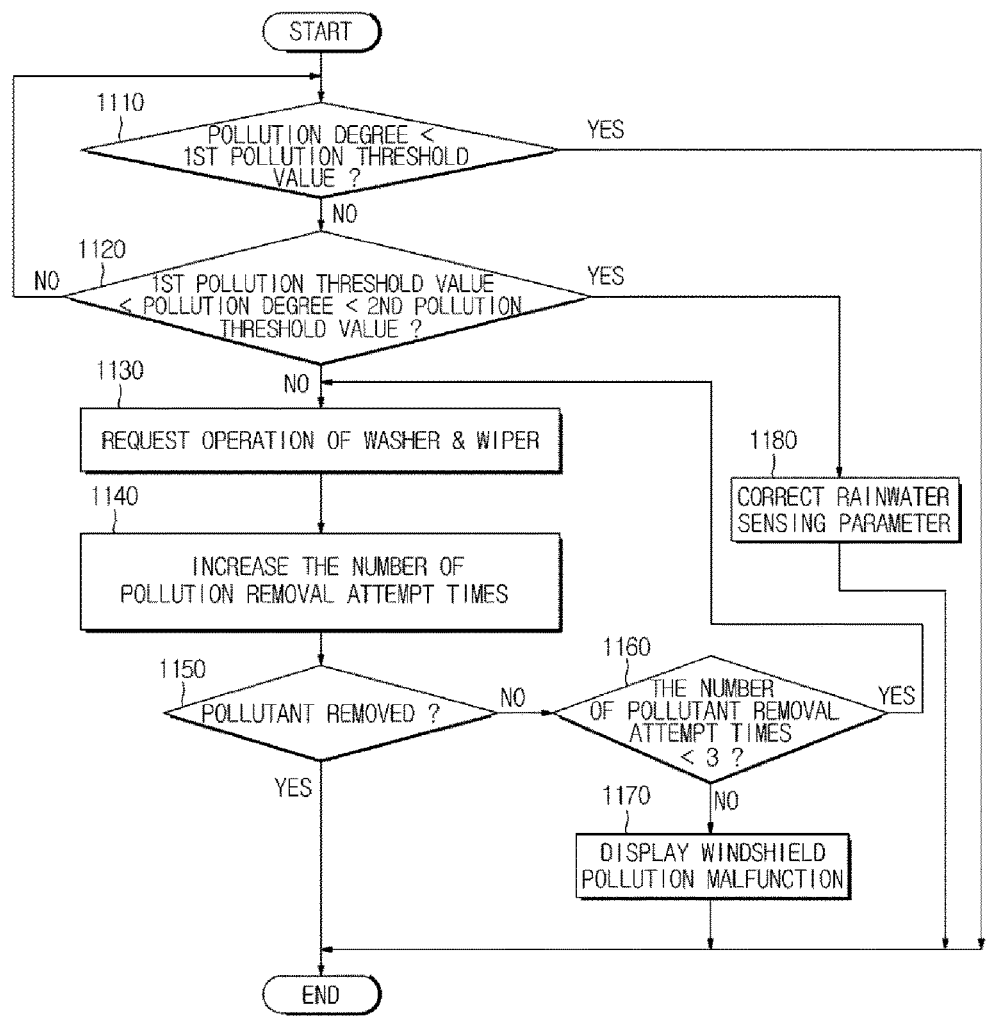

FIGS. 15 and 16 are flowcharts illustrating methods for determining the degree of pollution.

When an ignition signal IGN of the vehicle 1 is turned on (Operation 910), it is determined whether a current mode is an autonomous traveling mode (Operation 920). In this case, the operation 920 for determining whether a current mode is the autonomous traveling mode may herein be omitted according to the necessity of operators or administrators.

If the current mode is not identical to the autonomous traveling mode, the vehicle 1 may determine whether an automatic rain sensing state is decided (Operation 930). The operation 930 may be determined according to whether or not the washer 320 and the wiper 330 of the switch 600 are automatically established.

If the automatic rain sensing state is decided (Operation 930), the vehicle 1 may determine whether the initial ignition signal IGN is turned on (Operation 940).

If the initial ignition signal IGN is not turned on (Operation 940), the vehicle 1 may calculate the change amount of total-reflection reception light and the change amount of diffused-reflection reception light (Operation 950).

Subsequently, the vehicle 1 may calculate the degree of pollution on the basis of the calculation result (Operation 960). In this case, the reference for calculating the degree of pollution may be decided at random by operators or administers.

The vehicle 1 may determine the presence or absence of a polluted state on the basis of the calculation result (Operation 970).

If the polluted state is decided (Operation 970), the vehicle 1 may perform pollutant removal (Operation 980).

After the initial ignition signal IGN is turned on (Operation 940), when the vehicle 1 calculates the change amount of total-reflection reception light and the change amount of diffused-reflection reception light, the vehicle 1 may calculate the change amount of total-reflection reception light and the change amount of diffused-reflection reception light before/after starting the vehicle 1 (Operation 991).

Subsequently, when the degree of pollution is calculated, the pollution degree before starting the vehicle 1 and the pollution degree after starting the vehicle 1 may be calculated (Operation 993). In this case, the reference for calculating the pollution degree may be decided at random according to operators or administrators.

If the vehicle 1 determines the presence of a polluted state on the basis of the calculation results of the operations 960 and 993, the vehicle 1 may perform pollutant removal (Operation 980). In this case, the vehicle 1 may operate the washer 320 and the wiper 330.

FIG. 16 is a flowchart illustrating a method for determining whether a current state is a polluted state of FIG. 15, and illustrates the operations 970 and 980 for removing pollutants.

The vehicle 1 may determine whether the degree of pollution is less than a first pollution threshold value (i.e., a first pollution threshold value of FIG. 16) (Operation 1110).

If the pollution degree is not less than the first pollution threshold value (Operation 1110), the vehicle 1 may determine whether the pollution degree is higher than the first pollution threshold value and is less than a second pollution threshold value (i.e., a second pollution threshold value of FIG. 16) (Operation 1120).

If the pollution degree is higher than the first pollution threshold value and is not less than the second pollution threshold value (i.e., the second pollution threshold value of FIG. 16) (Operation 1120), the vehicle 1 may operate the washer 320 and the wiper 330 (Operation 1130). To this end, the vehicle 1 may also include the washer 320 and the wiper 330 without departing from the scope or spirit of the present disclosure.

Subsequently, the vehicle 1 may increase the number of pollutant removal attempt times (Operation 1140), and may determine whether the pollutants are completely removed on the basis of the amount of reception light of the light receiver 120 (Operation 1150).

If the pollutants are not completely removed (Operation 1150), the vehicle 1 may determine whether the number of pollutant removal attempt times is less than a reference number of times (e.g., three times) (Operation 1160).

If the number of pollutant removal attempt times is less than the reference number of times, the vehicle 1 may restart (or resume) from the operation 1130.

If the number of pollutant removal attempt times is higher than the reference number of times, the vehicle 1 may display information regarding a malfunction of windshield pollution such that the vehicle driver can recognize the malfunction information (Operation 1170).

If the pollution degree is higher than the first pollution threshold value and is less than the second pollution threshold value (i.e., the second pollution threshold value of FIG. 2) (Operation 1120), the vehicle 1 may correct a rainwater sensing reference value (i.e., a rainwater sensing parameter of FIG. 16) (Operation 1180).

Figure 17:
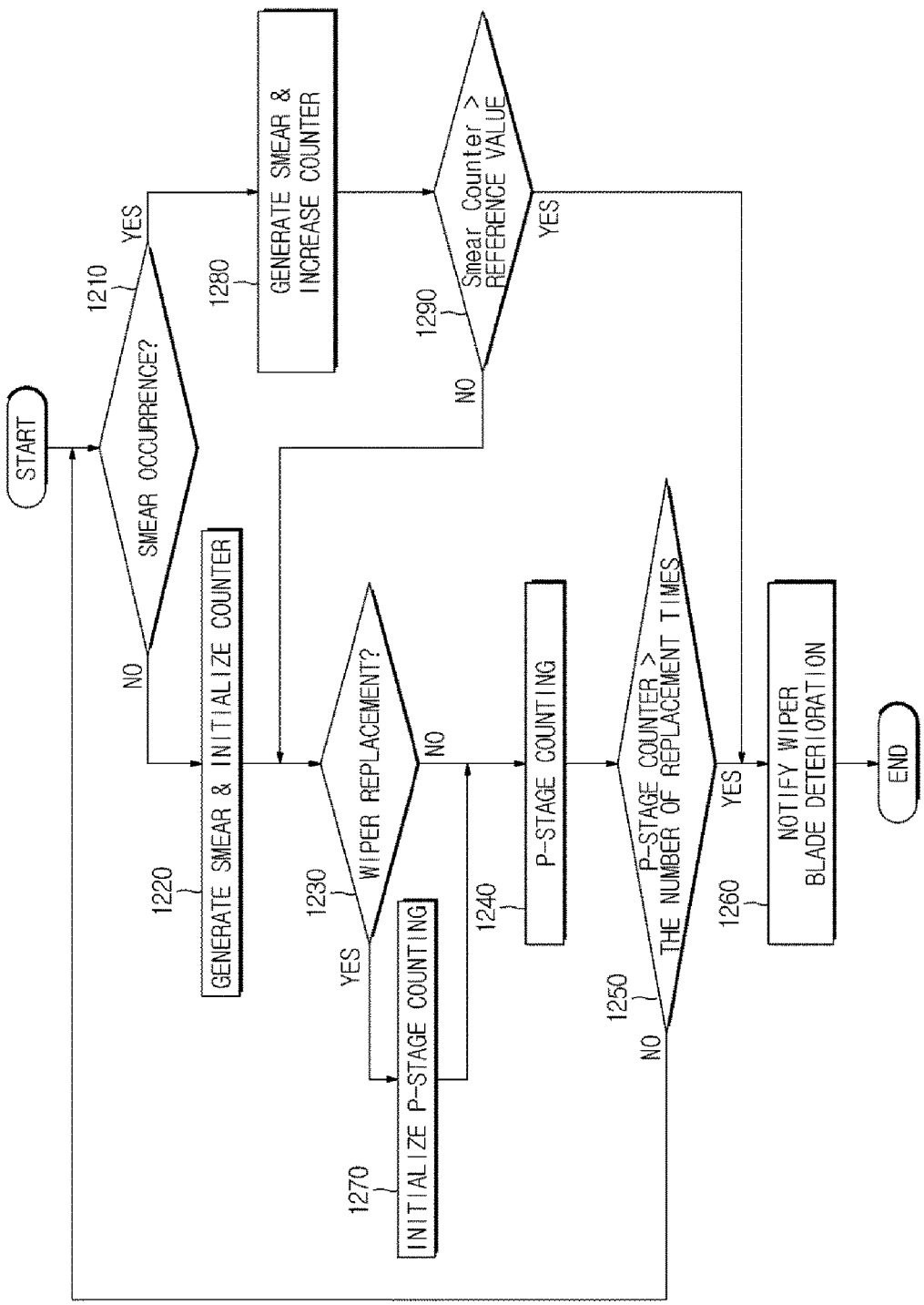
FIG. 17 is a flowchart illustrating a method for determining whether wiper blades need to be replaced.

FIG. 17 is a flowchart illustrating a method for determining whether wiper blades need to be replaced.

Referring to FIG. 17, the vehicle 1 may determine whether one or more smears occur (Operation 1210). In this case, the smear may indicate an oil film and unwashed pollutants or foreign substances.

After the wiper 330 performs the wiping action, if the amount of total-reflection reception light does not reach a reference value and is reduced by a predetermined offset, the vehicle 1 may determine the occurrence of smears.

If smears do not occur, the vehicle 1 may initialize a smear occurrence counter (Operation 1220).

The vehicle 1 may determine whether the wiper 330 has been replaced with a new one (Operation 1230). In this case, replacement or non-replacement of the wiper 330 may be determined through one case in which the wiper 330 is located at a service position or through the other case in which the vehicle driver manually inputs a wiper replacement command. In this case, the service position of the wiper may indicate that the wiper 330 of the vehicle 1 automatically moves upward to a specific position at which the wiper 330 can be automatically replaced and then stops.

If the wiper 330 is not replaced, the vehicle 1 may perform parking-stage (P-stage) counting (Operation 1240).

The vehicle 1 may determine whether the number of P-stage counting times is higher than a predetermined number of times needed for wiper replacement (Operation 1250).

If the number of P-stage counting times is higher than the predetermined number of times needed for wiper replacement, the vehicle 1 may display information regarding wiper blade replacement (operation 1260). In other words, although the smears are not generated, the vehicle 1 may detect deterioration of the wiper 330 such that the vehicle 1 may inform the vehicle driver that the wiper blades need to be replaced.

If the wiper 330 is replaced with a new one (Operation 1230), the vehicle 1 may initialize the P-stage counting (Operation 1270).

If the smear occurs (Operation 1210), the vehicle 1 may increase a value of the smear occurrence counter (Operation 1280).

Subsequently, the vehicle 1 may determine whether the smear counter is higher than a reference value (Operation 1290).

If the smear counter value is higher than the reference value, the vehicle 1 may inform the vehicle driver that the wiper blades need to be replaced (Operation 1260).

If the smear counter value is not higher than the reference value (Operation 1290), the vehicle 1 may start from the operation 1230.

The above-mentioned embodiments may be implemented in the form of a recording medium storing commands capable of being executed by a computer system. The commands may be stored in the form of program code. When the commands are executed by the processor, a program module is generated by the commands so that the operations of the disclosed embodiments may be carried out. The recording medium may be implemented as a computer-readable recording medium.

The computer-readable recording medium includes all kinds of recording media storing data readable by a computer system. Examples of the computer-readable recording medium include a Read Only Memory (ROM), a Random Access Memory (RAM), a magnetic tape, a magnetic disk, a flash memory, an optical data storage device, etc.

As is apparent from the above description, the rain sensor, the vehicle using the same, and the method for controlling the vehicle according to the embodiments can continuously monitor a windshield state to detect foreign substances and the degree of pollution, and can remove the foreign substances from the windshield by controlling constituent elements contained in the vehicle according to the detection result, such that a clean windshield is always maintained, resulting in a guarantee of the driver's field of vision.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. A rain sensor, comprising:
   a light transmitter configured to radiate light to a windshield of a vehicle;
   a light receiver configured to receive light reflected from the windshield to generate a reception light signal;
   a filter configured to filter out noise from the reception light signal; and
   a controller configured to determine a presence or absence of pollutant and a degree of pollution on the basis of the filtered reception light signal, and perform pollutant removing,
   wherein the light transmitter includes a total reflection light transmitter and a diffused reflection light transmitter, and wherein during short-term monitoring the controller compares each of an amount of total reflection reception light, which is received from the total reflection light transmitter and reflected, and an amount of diffused-reflection reception light, which is received from the diffused reflection light transmitter and reflected, with an amount of normal reception light of a normal state, so as to detect a difference among the amount of total reflection reception light, the amount of diffused-reflection reception light, and the amount of normal reception light, and detects an outdoor temperature, thereby detecting the presence or absence of the pollutant on the basis of the detected difference and the detected outdoor temperature.

2. The rain sensor according to claim 1, wherein the pollutant includes at least one of muddy water, snow, ice, dust and/or oil film.

3. The rain sensor according to claim 1, wherein:
   the controller long-term monitors the amount of total reflection reception light transmitted and reflected from the total reflection light transmitter and the amount of diffused reflection reception light transmitted and reflected from the diffused reflection light transmitter, and performs pollutant removing by reflecting the pollution degree when the pollution degree is equal to or higher than a reference value.

4. The rain sensor according to claim 3, wherein:
the controller determines the pollution degree by determining the pollution degree by long-term monitoring the amount of total reflection reception light and the amount of diffused reflection reception light, and corrects a rainwater sensing reference value according to the determined pollution degree.

5. The rain sensor according to claim 3, wherein:
the controller stores the long-term monitoring result of the total reflection reception light and the diffused reflection reception light, compares the amount of reception light before starting the vehicle with the amount of reception light after starting the vehicle so as to determine the pollution degree, and performs pollutant removing according to the determined result.

6. The rain sensor according to claim 1, wherein:
after completion of a wiping operation, if the amount of total reflection reception light transmitted and reflected from the total reflection light transmitter does not reach a reference value and is reduced by an offset, the controller determines that wiper blades need to be replaced, and performs wiper blade replacement notification.

7. The rain sensor according to claim 1, wherein:
the vehicle equipped with the rain sensor is an autonomous traveling mode, the controller determines the presence or absence of the pollutant and the degree of pollution, and performs pollutant removing according to the determined result.

* * * * *